US 8,156,210 B2

(12) United States Patent
Metz et al.

(10) Patent No.: US 8,156,210 B2
(45) Date of Patent: Apr. 10, 2012

(54) WORKFLOW FOR COMPUTER AIDED DETECTION

(75) Inventors: Stephen W. Metz, Greenfield, WI (US); Carson H. Thomas, Brookfield, WI (US); Fleming Y. M. Lure, Potomac, MD (US); Edward A. Martello, Glenwood, MD (US); Jyh-Shyan Lin, N. Potomac, MD (US)

(73) Assignees: GE Medical Systems Global Technology Company, Waukesha, WI (US); Riverain Medical Group, LLC, Dayton, OH (US)

( * ) Notice: Subject to any disclaimer, the term of this patent is extended or adjusted under 35 U.S.C. 154(b) by 1702 days.

(21) Appl. No.: 10/338,393

(22) Filed: Jan. 8, 2003

(65) Prior Publication Data

US 2004/0102689 A1    May 27, 2004

Related U.S. Application Data

(60) Provisional application No. 60/429,629, filed on Nov. 27, 2002.

(51) Int. Cl.
    *G06F 15/173* (2006.01)
(52) U.S. Cl. ........................................ 709/223; 382/132
(58) Field of Classification Search .................. 709/223; 382/132
    See application file for complete search history.

(56) References Cited

U.S. PATENT DOCUMENTS

| | | | | |
|---|---|---|---|---|
| 5,235,510 A | * | 8/1993 | Yamada et al. | 600/300 |
| 5,807,256 A | * | 9/1998 | Taguchi et al. | 600/425 |
| 7,505,614 B1 | * | 3/2009 | De La Torre-Bueno | 382/128 |
| 2001/0041991 A1 | * | 11/2001 | Segal et al. | 705/3 |
| 2002/0016821 A1 | * | 2/2002 | Son et al. | 709/204 |
| 2002/0029264 A1 | * | 3/2002 | Ogino et al. | 709/223 |
| 2002/0087359 A1 | * | 7/2002 | Bocionek | 705/2 |
| 2002/0114530 A1 | * | 8/2002 | Duarte | 382/254 |
| 2002/0133373 A1 | * | 9/2002 | Silva-Craig et al. | 705/2 |
| 2003/0110178 A1 | * | 6/2003 | Woods et al. | 707/100 |
| 2004/0024292 A1 | * | 2/2004 | Menhardt et al. | 600/300 |
| 2004/0068167 A1 | * | 4/2004 | Hsieh et al. | 600/407 |
| 2004/0077952 A1 | * | 4/2004 | Rafter et al. | 600/481 |
| 2004/0078238 A1 | * | 4/2004 | Thomas et al. | 705/3 |

OTHER PUBLICATIONS

Douglas E. Comer, "Computer Networks and Internets with Internet Applications", 2001. Prentice Hall, Third Edition.*
Lead Tools, "Overview: Basic DICOM File Structure", Jan. 19, 2010, p. 1-4.*

* cited by examiner

*Primary Examiner* — Ryan Jakovac
(74) *Attorney, Agent, or Firm* — McAndrews, Held & Malloy, Ltd.; William Baxter

(57) ABSTRACT

A method is disclosed, in a diagnostic medical environment, that enhances workflow while using a computer-aided-detection (or diagnosis) (CAD) system in the environment. The method comprises generating image data with a diagnostic medical imaging acquisition system. The image data is transmitted from the diagnostic medical imaging acquisition system to a computer-aided-detection (or diagnosis) (CAD) system and an archive/review station. Detection results are generated by processing the image data, using the CAD system, while storing and viewing the image data on the archive/review station. The detection results are transmitted from the CAD system to the archive/review station. The detection results are integrated with the image data by the archive/review station to form composite image data. The composite image data is displayed by the archive/review system.

25 Claims, 5 Drawing Sheets

Diagnostic Medical Environment

Fig. 1 --Prior Art--

WORKFLOW FOR COMPUTER AIDED DETECTION

RELATED APPLICATIONS

This application claims priority to and claims the benefit of U.S. Provisional Patent Application Ser. No. 60/429,629 filed on Nov. 27, 2002.

FEDERALLY SPONSORED RESEARCH OR DEVELOPMENT

[Not Applicable]

BACKGROUND OF THE INVENTION

Certain embodiments of the present invention relate to workflow in a diagnostic medical environment. More particularly, certain embodiments relate to enhancing the workflow in a diagnostic medical environment that uses computer-aided-detection (or diagnosis) (CAD) capability.

A typical diagnostic medical environment, such as a radiology department of a hospital, uses several different types of medical systems such as diagnostic medical imaging acquisition systems, and archive/review stations. The various types of medical systems may be standalone pieces or may be integrated together using one or more networks to improve synergy and workflow. For example, a Digital Imaging Communications in Medicine (DICOM)-based network interface may be used to integrate the various systems. DICOM is a network protocol that sits on top of TCP/IP on a network. The protocol includes a header having patient information and image category information. DICOM allows interoperability between the various medical systems and is able to pass both image data and reports between the systems.

DICOM is the standard in the radiology and cardiology imaging industry for the exchange and management of images and image related information between health systems that are developed independently of each other. DICOM is the healthcare standard for imaging data.

There are many different types of diagnostic medical imaging acquisitions systems that may be used in a diagnostic medical environment. Some examples are X-ray systems, magnetic resonance (MR) systems, computed tomography (CT) systems, positron emission tomography (PET) systems, and ultrasound systems.

Archive/review stations are often used to store large amounts of image data from the diagnostic medical imaging and acquisition systems and to display the image data to health care professionals, such as radiologists, in the form of images. An archive/review station typically comprises storage space and a database to manage the storage space. An archive/review station is typically software heavy and is able to query the database to call up and process stored image data.

Sometimes diagnostic medical environments incorporate a computer-aided-detection (or diagnosis) (CAD) system that processes and analyzes the image data before sending the image data to the archive/review station. FIG. 1 is an exemplary illustration of such an environment. Image data is passed over a network from the diagnostic medical imaging acquisition system to the CAD system.

The CAD system processes the image data, looking for physiological abnormalities in the image data such as, for example, cancerous tumors, lesions, broken bones, blood vessel blockage, tissue damage, bleeding, and other diseases. The CAD system produces detection results that may later be integrated with displayed image data to indicate the abnormal areas. A CAD system typically comprises a general image processing computer with specialized detection algorithms and software.

With the CAD system between the diagnostic medical imaging acquisition system and archive/review station as shown in FIG. 1, there may be a significant delay before the image data gets to the archive/review station. This may cause the health care professional to have to wait while the CAD system performs its processing and analysis. Particularly, if a problem arises, such as image data getting stuck in the CAD system due to a network problem, then the wait may be quite long while a service person is called. Poor workflow performance in the diagnostic medical environment results.

A basic need exists to improve the workflow performance in diagnostic medical environments employing computer-aided-detection (or diagnosis) (CAD) capability.

BRIEF SUMMARY OF THE INVENTION

An embodiment of the present invention provides for integrating a computer-aided-detection (or diagnosis) (CAD) system into a diagnostic medical environment without disrupting the workflow of the environment.

A method is provided which comprises generating image data with a diagnostic medical imaging acquisition system. The image data is transmitted from the diagnostic medical imaging acquisition system to a computer-aided-detection (or diagnosis) (CAD) system and to an archive/review station. Detection results are generated by processing the image data, using the CAD system, while storing and viewing the image data on the archive/review station. The detection results are transmitted from the CAD system to the archive/review station. The detection results are integrated with the image data by the archive/review station to form composite image data. The composite image data is displayed by the archive/review system.

Certain embodiments of the present invention afford an approach to enhance the workflow in a diagnostic medical environment that uses computer-aided-detection (or diagnosis) (CAD) capability.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION OF THE INVENTION

Figure 1:
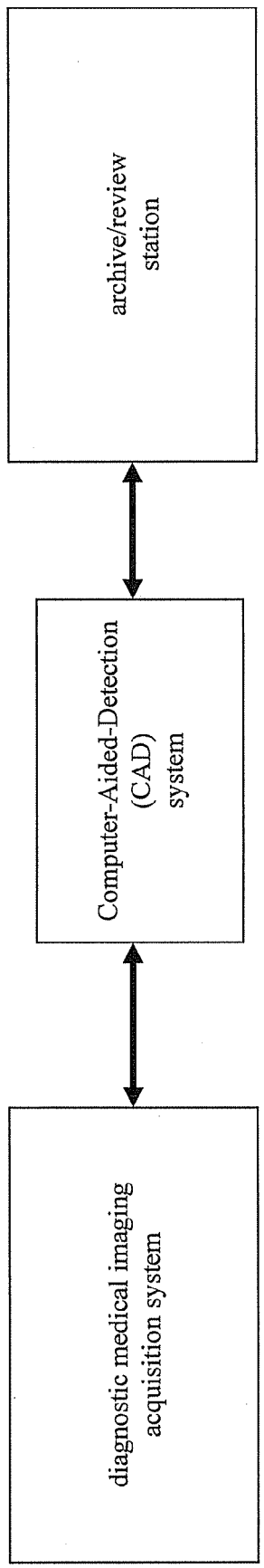
FIG. 1 illustrates a schematic block diagram of a medical diagnostic environment incorporating a computer-aided-detection (or diagnosis) (CAD) system between a diagnostic medical imaging acquisition system and an archive/review station.
Figure 2:
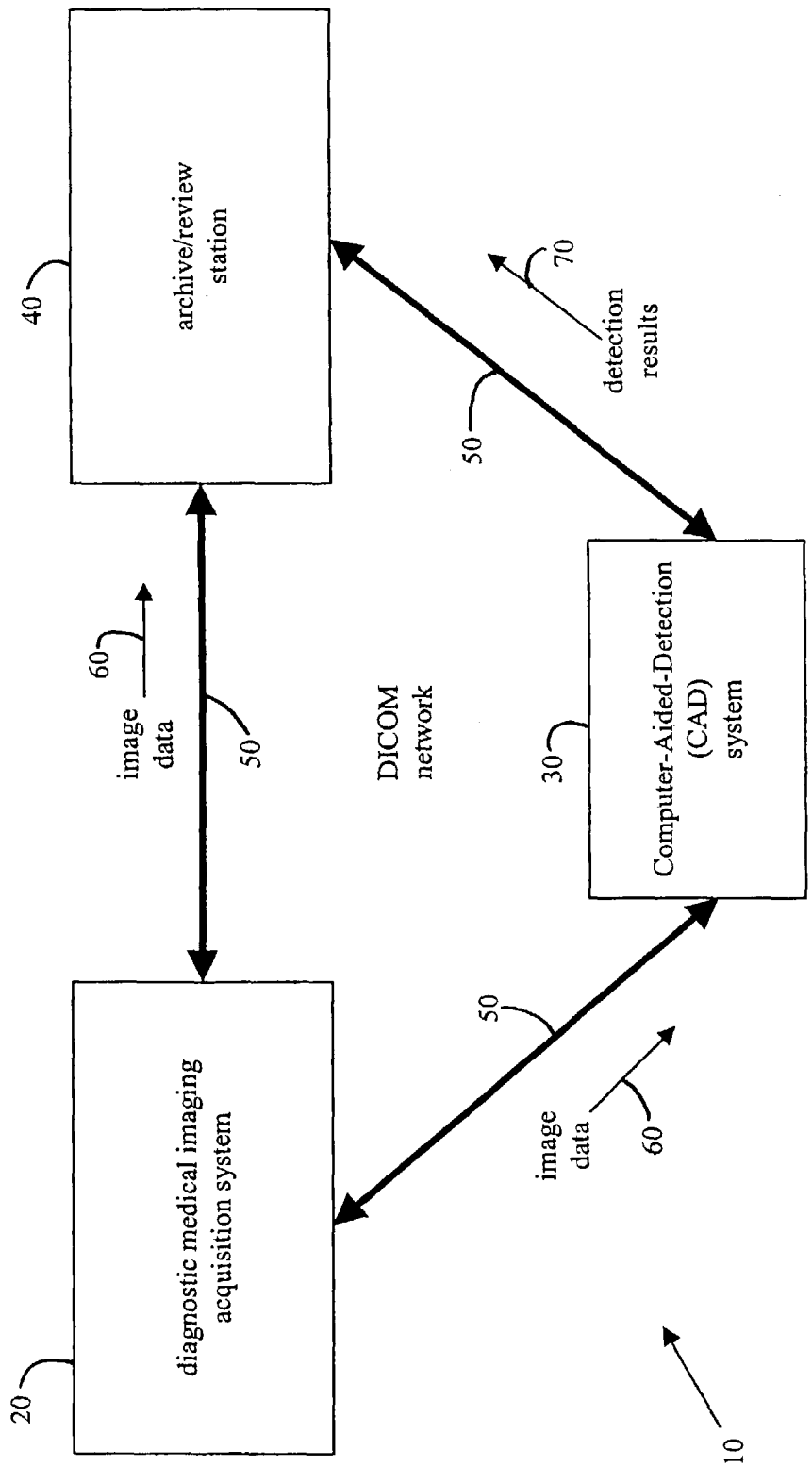
FIG. 2 is a schematic block diagram of a diagnostic medical environment incorporating a computer-aided-detection (or diagnosis) (CAD) system in accordance with an embodiment of the present invention.

An embodiment of the present invention enables enhanced workflow in a diagnostic medical environment. FIG. 2 is a schematic block diagram of a diagnostic medical environment 10 incorporating a computer-aided-detection (or diagnosis) (CAD) system 30 in accordance with an embodiment of the present invention.

The diagnostic medical environment 10 comprises a diagnostic medical imaging acquisition system 20, an archive/review station 40, and a computer-aided-detection (or diagnosis) (CAD) system 30 in accordance with an embodiment of the present invention. A network 50, interfaces the systems of the environment 10 to each other. The network 50 comprises a DICOM compatible network in accordance with an embodiment of the present invention. In accordance with an embodiment of the present invention, the acquisition system 20, archive/review station 40, and the CAD system 30 are all DICOM-compatible devices.

In accordance with an embodiment of the present invention, the network 50 is a bi-directional network able to communicate in both directions between linked systems.

Alternative embodiments of the present invention may comprise multiple diagnostic medical imaging acquisition systems and multiple archive/review stations. Also, alternative embodiments of the present invention may comprise multiple networks using different network protocols which may be the same as or different than DICOM.

Figure 3:
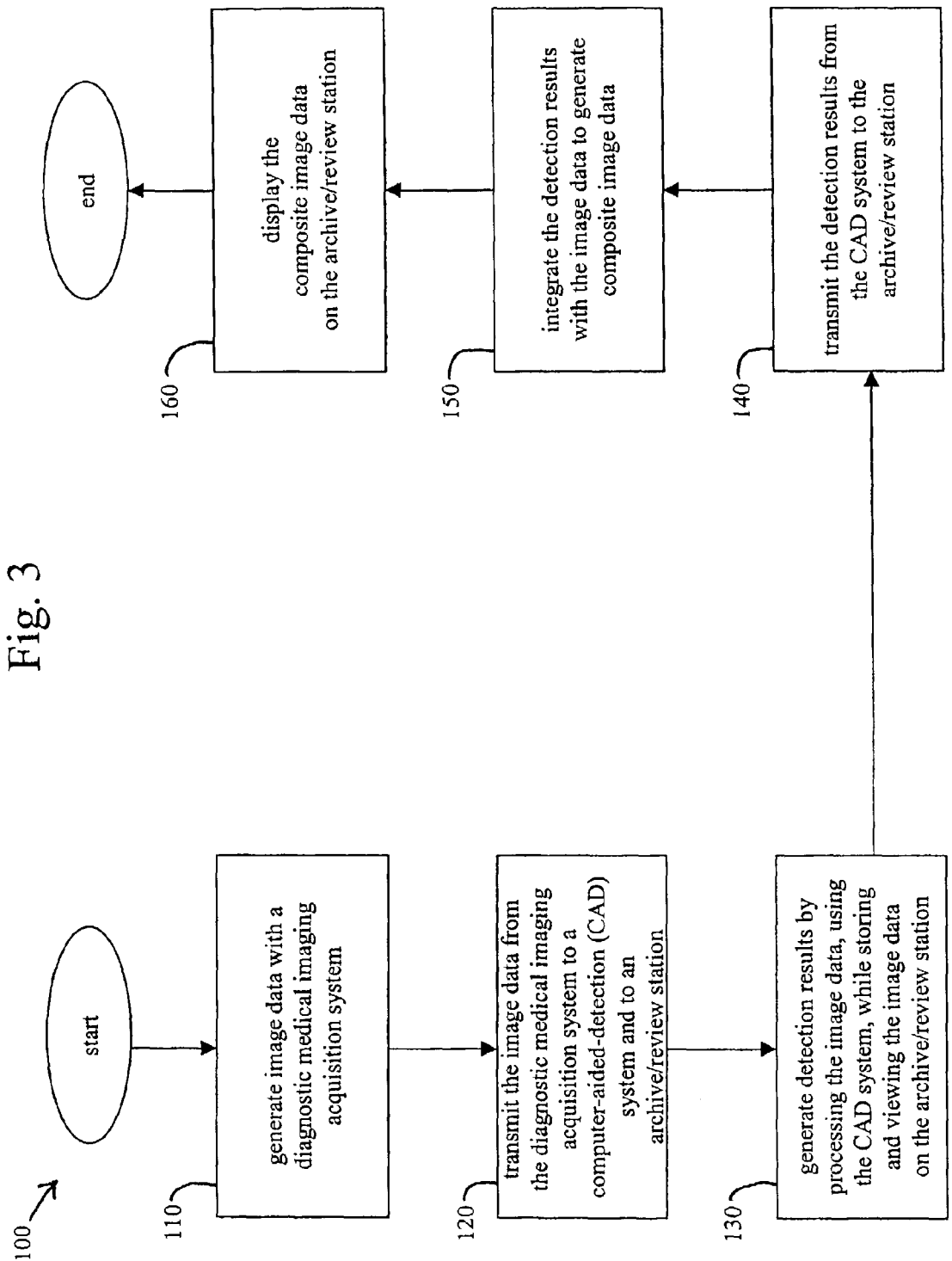
FIG. 3 is a flowchart of a method to improve a workflow process in the diagnostic medical environment of FIG. 2 in accordance with an embodiment of the present invention.

Referring to method 100 in FIG. 3, in step 110 the diagnostic medical imaging acquisition system 20 generates image data 60. Depending on the type of system 20, the image data 60 may comprise ultrasound image data, X-ray image data, CT image data, MR image data, or some other type of image data. In an embodiment of the present invention, the image data 60 is in a DICOM-compatible format comprising a header and the actual physiological image information.

In step 120, the image data is transmitted over the network 50 to both the CAD system 30 and the archive/review station 40. As a result, the image data 60 may be stored and displayed on the archive/review system 40 almost immediately without having to first wait for the image data 60 to pass through the CAD system 30.

In an embodiment of the present invention, the CAD system 30 is pre-configured to know what type of image data to look for and process. The CAD system 30 looks at the information in the header of the image data 60 to identify the image data and verify that it has received the correct image data to process. For example, in an embodiment of the present invention, the header data comprises image data source (what system the image data came from), anatomical type that the image data corresponds to (e.g., chest, abdomen, head), anatomical view of the image data (e.g., posterior, anterior, lateral).

In step 130, the CAD system 30 generates detection results 70 by processing the image data 60 using a detection algorithm. At the same time, the image data 60 is still being stored and viewed on the archive/review station 40. The CAD system 30 is looking for physiological abnormalities in the image data 60 such as, for example, cancerous masses, diseased tissue, lesions, broken bones, blood vessel blockage, tissue damage, and bleeding. The detection algorithm may be designed to handle a certain type of anatomy (e.g., chest) and look for a certain type of abnormality (e.g., cancerous masses). As an alternative, the detection algorithm may be designed to process multiple image types and look for multiple types of abnormalities.

Once the CAD system 30 has completed generating the detection results 70 then, in step 140, the CAD system 30 transmits the detection results to the archive/review station 40 in a DICOM-compatible format in accordance with an embodiment of the present invention. In step 150, the archive/review station 40 integrates the detection results 70 with the image data 60 to generate composite image data in accordance with an embodiment of the present invention.

In step 160, the archive/review station displays the composite image data as detection result symbols incorporated into resultant images of the image data 60 in accordance with an embodiment of the present invention. The detection results symbols may comprise, for example, text, geometric figures, arrows, colors, or some other type of indicia to indicate abnormalities in accordance with various embodiments of the present invention.

In alternative embodiments of the present invention, the detection results 70 may be in the form of stand-alone overlays, presentation states, a new instance of the image data 60 with the detection results 70 burned into the pixel data, or a new instance of a DICOM object that contains the derived information.

In an embodiment of the present invention, a user of the archive/review station 40 may turn the detection results on and off to display or not display the detection result symbols in conjunction with the image data.

In another alternative embodiment of the present invention, the detection results 70 may be integrated with the image data 16 in the CAD system 30. Then, the resultant composite image data may be transmitted to the archive/review station 40 for subsequent display.

Figure 4:
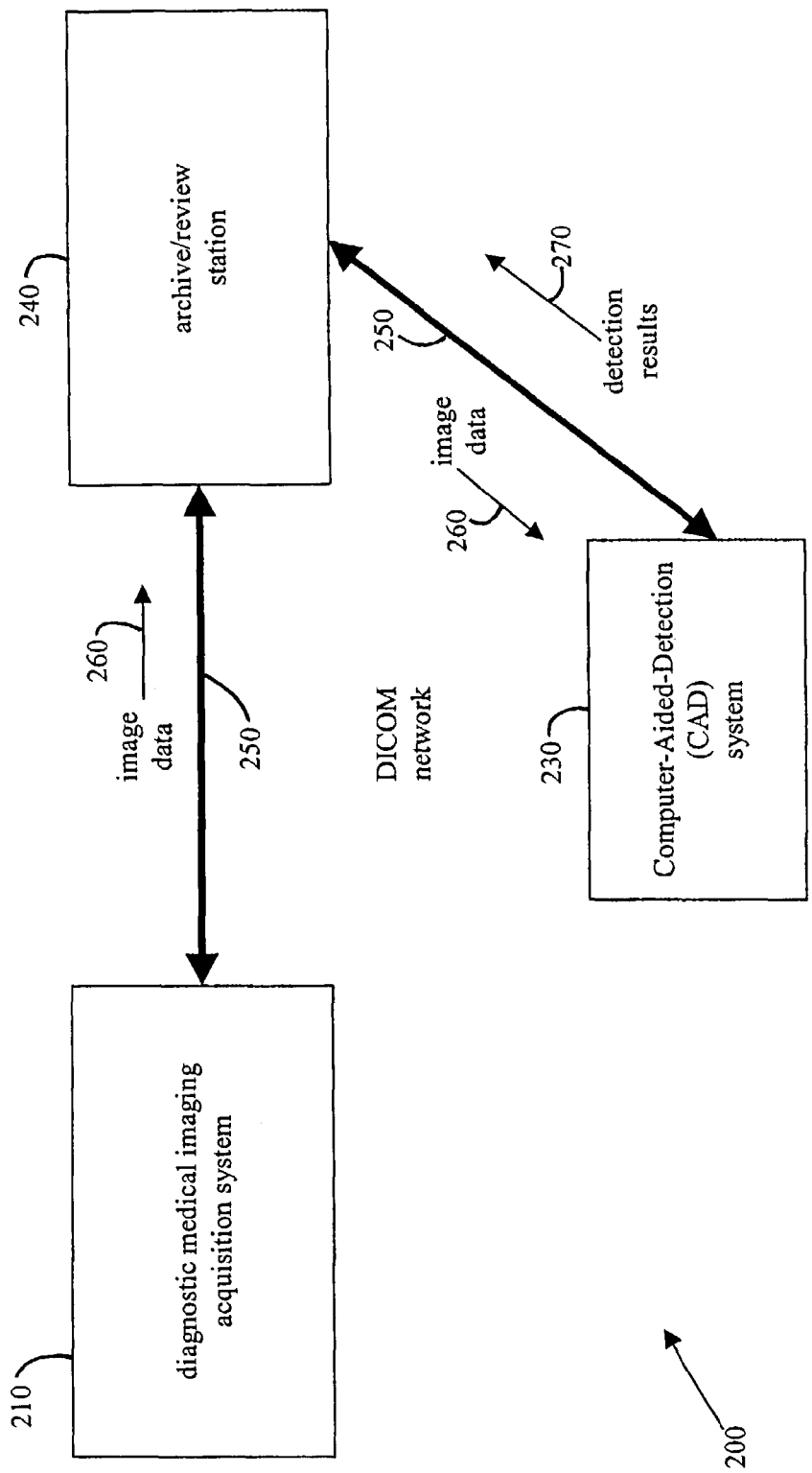
FIG. 4 is a schematic block diagram of an alternative diagnostic medical environment incorporating a computer-aided-detection (or diagnosis) (CAD) system in accordance with an embodiment of the present invention.

FIG. 4 illustrates a schematic block diagram of an alternative diagnostic medical environment 200 incorporating a computer-aided-detection (or diagnosis) (CAD) system 230 in accordance with an embodiment of the present invention. The environment 200 further comprises a diagnostic medical acquisition system 210 and an archive/review station 240. However, the network 250 does not pass image data 260 to both the archive/review station 240 and the CAD system 230 from the diagnostic medical imaging acquisition system 210.

Figure 5:
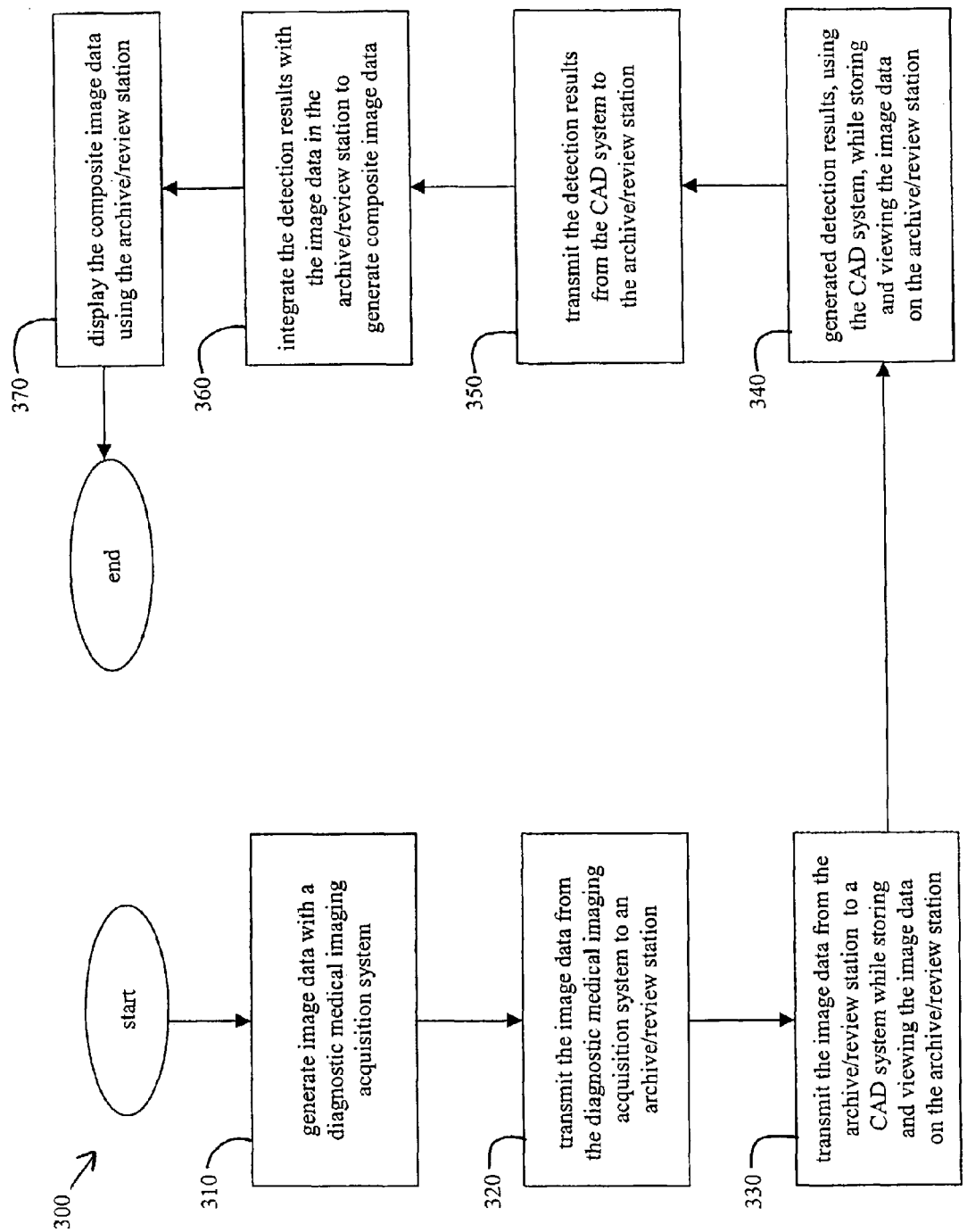
FIG. 5 is a flowchart of an alternative method to improve a workflow process in the alternative diagnostic medical environment of FIG. 4 in accordance with an embodiment of the present invention.

Referring to the method 300 of FIG. 5, in step 310, the diagnostic medical imaging acquisition system 210 generates image data 260 as before. But in step 320, the diagnostic medical imaging acquisition system 210 transmits the image data 260 only to the archive/review station 240 over the network 250, and not to the CAD system 230 as before. Instead, in step 330, the image data 260 is transmitted from the archive/review station 240 to the CAD system 230 over the network 250 while storing and viewing the image data 260 on the archive/review station 240.

In step 340, the CAD system again generates detection results 270 by processing the image data 260 while the image data 260 is still stored and being viewed on the archive/review station 240. In step 350, the detection results 270 are transmitted from the CAD system 230 to the archive/review station 240 over the network 250.

In step 360, the detection results 270 are integrated with the image data 260 as before by the archive/review station 240 to generate composite image data. The composite image data may be displayed, in step 370, as before.

The alternative method 300 is not quite as efficient as the method 100 since there is not a network interface directly between the diagnostic medical imaging acquisition system 210 and the CAD system 230 in environment 200. Method 300 requires seven steps whereas method 100 requires only 6 steps as previously described.

The alternative embodiments previously described for environment 10 and method 100 apply equally as well to environment 200 and method 300.

In summary, certain embodiments of the present invention afford an approach to improve the workflow in a diagnostic medical environment employing computer-aided-detection (or diagnosis) (CAD) technology. Image data may be sent directly from a diagnostic medical imaging acquisition system to both a CAD system and an archive/review station in order to immediately store and view the image data on the archive/review station instead of first waiting for the CAD system to generate detection results.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In a diagnostic medical environment, a method to efficiently incorporate computer-aided-detection (CAD) capability into a workflow process of said diagnostic medical environment, said method comprising:
   transmitting image data from at least one diagnostic medical imaging acquisition system to at least a computer-aided-detection (or diagnosis) (CAD) system and at least one archive/review station;
   generating computer-aided-detection results by processing said image data to detect abnormalities in the image data, using said CAD system, while archiving and viewing said image data on at least said at least one archive/review station; and
   transmitting said computer-aided-detection results from said CAD system to at least said at least one archive/review station,
   wherein said transmitting image data and said transmitting said computer-aided-detection results are performed in a DICOM format and over a network connected between said at least one diagnostic medical imaging acquisition system, said CAD system, and said at least one archive/review station.

2. The method of claim 1 further comprising generating said image data with said at least one diagnostic medical imaging acquisition system.

3. The method of claim 1 further comprising integrating said computer-aided-detection results with said image data, using said at least one archive/review station, to generate composite image data.

4. The method of claim 3 further comprising displaying said composite image data using said at least one archive/review station.

5. The method of claim 3 wherein said computer-aided-detection results are indicated within said composite image data by at least one of text, arrows, geometrical symbols, and colors.

6. The method of claim 1 further comprising supporting a DICOM protocol over said network.

7. The method of claim 1 wherein said at least one diagnostic medical imaging acquisition system comprises at least one of an X-ray system, a CT system, an ultrasound system, an MR system, a film scanning device, and a PET system.

8. The method of claim 1 wherein said CAD system is pre-configured to identify and process certain categories of image data.

9. The method of claim 1 further comprising verifying certain identifiers associated with said image data using said CAD system.

10. The method of claim 9 wherein said certain identifiers comprise at least one of image data source, anatomical type, and anatomical view.

11. The method of claim 9 wherein said certain identifiers are embedded in at least one header of said image data.

12. The method of claim 1 wherein said abnormalities identified in said computer-aided-detection results correspond to physiological abnormalities depicted in said image data.

13. The method of claim 12 wherein said physiological abnormalities comprise at least one of cancerous masses, diseased tissue, lesions, broken bones, blood vessel blockage, tissue damage, and bleeding.

14. The method of claim 1 wherein said at least one diagnostic medical imaging acquisition system comprises a DICOM compatible device.

15. The method of claim 1 wherein said CAD system comprises a DICOM compatible device.

16. The method of claim 1 wherein said at least one archive/review station comprises a DICOM compatible device.

17. The method of claim 1 further comprising bi-directionally communicating over said network between said at least one diagnostic medical imaging acquisition system and said CAD system.

18. The method of claim 1 further comprising bi-directionally communicating over said network between said at least one diagnostic medical imaging acquisition system and said at least one archive/review station.

19. The method of claim 1 further comprising bi-directionally communicating over said network between said CAD system and said at least one archive/review station.

20. The method of claim 3 wherein said computer-aided-detection results may be eliminated or added to a display of said composite image data by a user of said at least one archive/review station.

21. The method of claim 1 wherein said image data comprises at least header information and physiological image information in a DICOM-compatible format.

22. In a diagnostic medical environment, a method to efficiently incorporate computer-aided-detection (or diagnosis) (CAD) capability into a workflow process of said diagnostic medical environment, said method comprising:
   transmitting image data from at least one diagnostic medical imaging acquisition system to at least one archive/review station;
   transmitting said image data from said archive/review station to a computer-aided-detection (or diagnosis) (CAD) system while archiving and viewing said image data on said at least one archive/review station;
   generating computer-aided-detection results by processing said image data to detect abnormalities in the image data using said CAD system while archiving and viewing said image data on said at least one archive/review station; and
   transmitting said computer-aided-detection results from said CAD system to said at least one archive/review station,
   wherein said transmitting image data is performed in a DICOM format and over a network connected between said at least one diagnostic medical imaging acquisition system and said at least one archive/review station, wherein said transmitting said image data and said transmitting said computer-aided-detection results are performed in a DICOM format and over a network connected between said CAD system and said at least one archive/review station.

23. The method of claim 22 further comprising generating said image data with said at least one diagnostic medical imaging acquisition system.

24. The method of claim 22 further comprising integrating said computer-aided-detection results with said image data, using said archive/review station, to generate composite image data.

25. The method of claim 24 further comprising displaying said composite image data using said archive/review station.

* * * * *